(12) United States Patent
Lefevre et al.

(10) Patent No.: US 7,638,290 B2
(45) Date of Patent: Dec. 29, 2009

(54) REAGENT AND PROCESS FOR THE IDENTIFICATION AND COUNTING OF BIOLOGICAL CELLS

(75) Inventors: Didier Lefevre, Saint Clement de Riviere (FR); Sylvie Veriac, Montpellier (FR); Henri Champseix, Saint Gely du Fesc (FR)

(73) Assignee: ABX (FR)

(*) Notice: Subject to any disclaimer, the term of this patent is extended or adjusted under 35 U.S.C. 154(b) by 348 days.

(21) Appl. No.: 11/647,268

(22) Filed: Dec. 29, 2006

(65) Prior Publication Data

US 2007/0111276 A1    May 17, 2007

Related U.S. Application Data

(62) Division of application No. 10/081,118, filed on Feb. 25, 2002, now abandoned.

(30) Foreign Application Priority Data

Feb. 23, 2001 (FR) .................................. 01 02489

(51) Int. Cl.
G01N 33/567 (2006.01)
(52) U.S. Cl. .............................. 435/7.21; 435/2; 435/6; 435/7.25; 435/285.2; 435/173.5; 435/173.7; 436/522; 436/546; 436/8; 436/10; 436/17; 436/18; 436/172; 436/175; 436/176; 422/68.1; 422/73; 422/82.02; 422/82.05; 422/82.07; 422/82.09; 422/98
(58) Field of Classification Search .................... 436/2, 436/6, 7.21, 7.24, 7.25, 40.5, 285.2, 173.5, 436/173.7, 522, 546, 8, 10, 17, 18, 63, 164, 436/165, 169, 172, 175, 176, 177, 174; 422/51, 422/55, 73, 82.02, 82.07, 98, 68.1, 82.05, 422/82.09; 435/2, 6, 7.21, 7.24, 7.25, 7.5, 435/40.5, 285.2, 173.5, 173.7
See application file for complete search history.

(56) References Cited

U.S. PATENT DOCUMENTS 4,751,179 A    6/1988    Ledis et al.
5,232,857 A    8/1993    Lefevre et al.
5,496,734 A *  3/1996    Sakata ........................ 436/63
5,648,225 A    7/1997    Kim et al.
5,939,326 A *  8/1999    Chupp et al. ................. 436/63
5,994,138 A *  11/1999   Veriac ........................ 436/10
6,271,035 B1   8/2001    Deka et al.
6,562,563 B1   5/2003    Murphy et al.

FOREIGN PATENT DOCUMENTS

EP    0 343 380    4/1989
FR    2 759 166    8/1998

OTHER PUBLICATIONS

Haas et al., Cation-Anion Cotransport, Methods in Enzymology, 173:280-91 (1989) Abstract.
Lawrence R. Adams, et al., "Fluorometric Characterization of Six Classes of Human Leukocytes" Acta Cytol, vol. 18, No. 5, pp. 389-391, 1974.
Howard M. Shapiro et al., "Combined Blood Cell Counting and Classification with Fluorochrome Stains and Flow Instrumentation", J. Histochem Cytochem, vol. 24, No. 1, pp. 396-411, 1976.
Leon W.M.M. Terstappen et al., "Multidimensional Flow Cytometric Blood Cell Differentiation Without Erythrocyte 30 Lysis", Blood Cells, vol. 17, pp. 585-602, 1991.
Leon W.M.M. Terstappen et al., "Bone Marrow Cell Differential Counts Obtained by Multidimensional Flow Cytometry", Blood Cells, vol. 18 (2), pp. 311-330, 1992.
F. Traganos, et al., "Simultaneous Staining of Ribonucleic and Deoxyribonucleic Acids in Unfixed Cells Using Acridine Orange in a Flow Cytofluorometric System", The Journal of Histochemistry and Cytochemistry, vol. 25, No. 1, pp. 46-56, 1977.
Alan Pollack et al., "Flow Cytometric Analysis of RNA Content in Different Cell Populations Using Pyronin Y and Methyl Green", Cytometry, vol. 3, No. 1, pp. 28-35, 1982.

* cited by examiner

*Primary Examiner*—Gailene R Gabel

(57) ABSTRACT

The invention relates to a reagent and a process for the identification and counting of biological cells in a sample. This reagent comprises a cell lysing agent selected from at least one detergent in a concentration capable of specifically lysing a given type of cells in the sample, and a stain capable of marking the intracellular nucleic acids of the remaining unlysed cells. Application in particular for the identification and counting of cells using an automated analysis system based on flow cytometry.

15 Claims, 3 Drawing Sheets

REAGENT AND PROCESS FOR THE IDENTIFICATION AND COUNTING OF BIOLOGICAL CELLS

CROSS REFERENCE TO RELATED APPLICATIONS

This application is a Divisional of application Ser. No. 10/081,118 (abandoned), filed on Feb. 25, 2002, and for which priority is claimed under 35 U.S.C. § 120; and this application claims priority of Application No. 102489 filed in France on Feb. 23, 2001 under 35 U.S.C. § 119; the entire contents of all are hereby incorporated by reference.

FIELD OF THE INVENTION

The present invention relates to biological analyses and in particular to blood analyses.

The invention relates more particularly to a reagent and a process for the identification and counting of biological cells in a sample, in particular in a blood sample.

The biological sample may be human or animal blood, or also any other biological liquid or biological preparation.

BACKGROUND OF THE INVENTION

In the field of biological analyses the importance of the determination and precise counting of different cell populations in making a diagnosis has been recognised for a long time. In fact, the appearance of abnormal equilibrium ratios among normal cell populations in blood may be correlated with the appearance of certain medical conditions, for example immune reactions, inflammatory reactions, etc. Similarly, the appearance of abnormal cell populations may also be correlated with the appearance of other conditions, such as leukaemia, etc.

There are various conventional methods of cytological analysis, involving microscopic examination after staining, and if necessary after sedimentation or aggregation. The automatic determination of blood cells began at the beginning of the 1960s with the separation of the main normal leucocyte populations; see the following bibliographic reference: (1) Hallerman L., Thom R., Gerhartz H.: "Elecktronische Differentialzählzung von Granulocyten und Lymphocyten nach intervaler Fluochromierung mit Acridinorange" ("Electronic Differential Counting of Granulocytes and Lymphocytes by Interval Fluorochrome Staining with Acridine Orange"), Verh Deutsch Ges Inn Med 70: 217, 1964.

The separation of the leucocytes was performed by flow cytometry utilising various principles involving the optical and chemical properties of the cells. Several automated haematology analysers have been produced, using various techniques such as Coulter's principle for determining volumes, measurement of diffracted light for estimating sizes, measurement of diffused light at 90° for determining the internal structures of cells, and fluorescence or absorption measurements for determining the affinities of cells for various stains; see the following bibliographic references 2 to 5:

(2) Adams L. R., Kamensky L. A.: "Fluorometric Characterization of Six Classes of Human Leukocytes" Acta Cytol 18: 389, 1974;

(3) Shapiro H. M. et al. "Combined Blood Cell Counting and Classification with Fluorochrome Stains and Flow Instrumentation" J. Histochem Cytochem 24: 396-41.1, 1976;

(4) Terstappen L. W. et al. "Multidimensional Flow Cytometric Blood Cell Differentiation Without Erythrocyte Lysis" Blood Cells 17: 585-602, 1991;

(5) Terstappen L. W., Levin J. "Bone marrow cell differential counts obtained by multidimensional flow cytometry" Blood Cells 18 (2): 311-30, 1992.

The characterisation of cells in early stages of the cell cycle has long been of interest to scientists and the quantification of the RNA content of each cell has for a long time been recognised as a representative parameter of this cycle; see the bibliographic references 2 to 5 above and the following bibliographic references 6 and 7:

(6) Traganos F., Darzynkiewicz Z., Sharpless T., Melamed M. R. "Simulataneous Staining of Ribonucleic and Deoxyribonucleic Acids in Unfixed Cells Using Acridine Orange in a Flow Cytofluorometric System" J. Histochem Cytochem 25: 46, 1977; (7) Pollack A. et al. "Flow Cytometric Analysis of RNA Content in Different Cell Populations Using Pyronin Y and Methyl Green" Cytometry, vol. 3, no. 1, pages 28-35, 1982.

In their French patent no. 97 01090, dated 31 Jan. 1997, the Applicants have already described a composition, and more particularly a staining reagent, enabling this type of analysis to be performed.

In order to automate such techniques various problems first of all have to be solved, in particular reducing the treatment times and cost of preparing the samples. Such a reduction may be achieved in various ways, the most obvious being to reduce the number of channels so that only one cell preparation is carried out at any one time. This type of technique has previously been described by Léon W. Terstappen (reference 4 above), but requires a long treatment and analysis time, in particular for the accurate counting of the nucleate cells, the number of which is often a thousand times less than the number of erythrocytes.

In order to obviate this difficulty the biological sample is often separated into at least two aliquot parts, one of which is prepared at a certain concentration enabling the erythrocytes and platelets to be studied, the other being prepared at a higher concentration for the analysis of the nucleate cells.

These known techniques have various disadvantages.

Before the analysis, the treatment of this aliquot part often involves the specific destruction of the erythrocytes in order to facilitate the measurement of the remaining cells. Although such a method enables the results of the measurements to be obtained more quickly, this is nevertheless offset by the time involved in the reaction, transfer and staining in order to obtain the desired preparation.

The incubation time of a cell suspension in a reagent solution is in particular associated with the time required for the active principles to penetrate the interior of the cells. In French patent no. 97 01090 mentioned hereinbefore, the Applicants have described ways of accelerating this penetration involving the use of an additive, in particular an ionophore type additive, to assist the cell penetration.

The treatment time is also a function of the number of successive stages that the aliquot part has to pass through. Lysis and staining of the cells are often carried out in two successive stages, in one order or the other (see U.S. Pat. No. 6,004,816).

These two dilution stages involve a not inconsiderable expenditure in material, associated with a long minimum treatment time.

BRIEF SUMMARY OF THE INVENTION

An object of the present invention is accordingly to provide a reagent for the identification and counting of biological cells that avoids the aforementioned disadvantages.

An object of the present invention is in particular to provide such a reagent that enables the lysis of certain cells, in particular erythrocytes, the fixing of the nucleate cells and the staining of the intracellular material to be carried out simultaneously.

An object of the present invention is also to provide such a reagent that enables these operations to be carried out in a conveniently short time in order to reduce to a large extent the cost and time of the analysis and the number of reagents involved.

The invention accordingly provides a reagent for the identification and counting of biological cells in a sample, the said reagent comprising:
  a cell lysing agent selected from at least one detergent in a concentration sufficient to lyse specifically a given type of cell in the sample, and
  a stain designed to mark the intracellular nucleic acids of the remaining unlysed cell.

The invention thus provides a reagent for the simultaneous lysing and staining of a biological sample, enabling a solution of cells to be obtained in a single stage that can be analysed by for example a flow cytometry system. This analysis enables the thus treated cells to be classified and counted.

The reagent of the invention accordingly combines a reagent solution of the type described in French patent no. 97 01090 with a cell lysing agent that enables a given type of cells of the sample, in particular erythrocytes, to be specifically lysed.

The staining reagent solution per se, described in French patent no. 97 01090, enables the membrane permeation to be accelerated for the subsequent staining of the biological cells of the sample. This staining solution may be used before as well as after the lysing of the erythrocytes, depending on the types of cells being studied. The reagent principle of this staining solution is thus preserved and introduced into a lysing solution, enabling the erythrocytes to be destroyed and the remaining cells to be stained before they are counted.

The cell lysing agent advantageously includes at least one ionic and/or non-ionic detergent in a concentration capable of lysing erythrocytes.

The detergent of the invention is advantageously selected from:
  primary amines, amine acetates and hydrochlorides, quaternary ammonium salts, and trimethylethyl ammonium bromide;
  amides of substituted diamines, diethanolaminopropylamine or diethylaminopropylamide, amides of cyclised diethylenetriamine;
  alkylaryl sulfonates, petroleum sulfonates, sulfonated glycerides;
  cholamides, sulfobetaines;
  alkyl glycosides, saponins;
  polyoxyethylene ethers and sorbitans, polyglycol ethers.

In one embodiment this detergent comprises a mixture of TRITON X100® (polyethylene glycol tert-octylphenyl ether) in a concentration of 0.05% (w/v) and TWEEN 20® (polyoxyethylenesorbitan monolaurate) in a concentration of 0.0001% (v/v).

Throughout the description the expression "w/v" denotes "weight/volume" and the expression "v/v" denotes "volume/volume".

The stain that is used is advantageously of the fluorescent type.

Advantageously a stain is selected that is capable of combining specifically with the intracellular ribonucleic acid and enhancing its fluorescence once it has combined with the latter.

The stain of the invention may be selected in particular from the following stains:
thiazole orange or 1-methyl-4-[(3-methyl-2-(3H)-benzothiazolylidene)methyl]quinolinium p-tosylate,
thiazole blue,
4-[(3-methyl-2-(3H)-benzothiazolylidene)methyl]-1-[3-(trimethylammonium)propyl]quinolinium diiodide,
3,3'-dimethyloxacarbocyanine iodide or 3-methyl-2-[3(3-methyl-2(3H)-benzothiazolylidene-1-propenyl]benzoxazolium
iodide,
thioflavine T,
the stains SYTO® and TOTO® (TM Molecular Probes),
ethidium bromide,
propidium iodide,
acridine orange,
coriphosphine O,
auramine O,
the stains HOECHST 33258 (2'-(4-hydroxyphenyl)-5-(4 methyl-1-piperizinyl)-2,5'-bi-1H-benzimidazole trihydrochloride hydrate) and HOECHST 33342® (2'-(4-ethoxyphenyl)-5-(4-methyl-1-piperizinyl)-2,5'-bi-1H-benzimidazole trihydrochloride),
4' 6-diamino-2-phenylindole dihydrochloride (DAPI),
4' 6-(diimidazolin-2-yl)-2-phenylindole dihydrochloride (DIPI),
7-aminoactinomycin D,
actinomycin D, and
LDS 751 (2-(4-(4-dimethylaminophenyl)-1,3-butadienyl)-3-ethylbenzothiazolium perchiorate).

In a preferred embodiment of the invention the reagent moreover comprises at least one membrane penetration agent capable of promoting the penetration of the stain into the cells to be marked.

The agent promoting the membrane penetration is advantageously an ionophore compound of the protonophore and/or antibiotic type.

This agent is generally present in a concentration of less than 0.005% (w/v). An example of an antibiotic that can be used is valinomycin.

It is advantageous if the reagent moreover comprises at least one membrane fixing agent present in a concentration of 0.1% to 10% (w/v). This fixing agent preferably comprises at least one alcohol and/or one aldehyde. Paraformaldehyde or glutaraldehyde for example are preferably used for this purpose.

It is also possible within the scope of the invention to include other additives or components in the reagent.

This reagent may accordingly also comprise at least one compound selected from a complexing agent, an inorganic salt and a buffer system.

According to another aspect, the invention relates to a process for the identification and counting of biological cells in a sample, in particular in a blood sample, which process comprises the following operations:
  mixing and incubating the sample with a reagent as defined above in order to effect, in a single stage, the lysis of cells of a given type, in particular erythrocytes, the staining of the intracellular nucleic acids, and the fixing of the nucleate cells;

measuring the resultant solution by flow cytometry using at least two measuring parameters selected from resistive volume, axial luminous diffraction, axial luminous transmission, orthogonal light scattering, and fluorescence; and classifying and counting the nucleate cells in populations by means of the measured parameters.

In the flow cytometry measurement the axial luminous diffraction parameter is at least one parameter selected from small angle diffraction and large angle diffraction.

This measurement may be carried out by means of a flow cytometer having the conventional parameters such as axial diffraction or "FSC" (forward scatter), orthogonal diffusion or "SSC" (side scatter), either orthogonal fluorescence (FL1), axial fluorescence or epi-fluorescence, all polarised or depolarised, as well as additional measuring parameters such as transmitted light measurement or resistive volume as described in French patent no. 89 14120 of 27 Oct. 1989.

The resistivity may be measured by means of a continuous current in order to express the volume of the elements and/or by means of a pulsed or alternating current in order to express the internal densimetric differences approximating to the determination of the structure.

These parameters may be used to obtain sets of multi-parameter data for each of the analysed cells, enabling the latter to be classified. The classification will be more precise the more relevant and numerous the parameters defining the cells. This type of multi-parameter study has already been described before (see the bibliographic references 4 and 5 above).

Within the scope of the invention the classified nucleate cells may either be mature or immature, or normal or abnormal cells.

The classification of nucleate cells is carried out by known processes. The classification may be performed by means of a multidimensional analysis software program, with or without the use of a software or other neuronal technique.

Within the scope of the invention the biological sample may be a sample of a human or animal blood, or also a sample of biological fluid or a suspension of cells of human or animal origin.

This sample is mixed with the reagent solution under specified temperature conditions. The reaction kinetics mean that the erythrocytes are first of all destroyed, the penetration of the stain being in parallel to the fixing of the cells, which takes place more slowly.

DETAILED DESCRIPTION OF THE INVENTION

The invention will now be described by reference to the following example:

Example

Within the scope of this example a reagent is used having the following composition:

| Complexing agent | EDTA | 0.02% (w/v) |
|---|---|---|
| Inorganic salt | NaCl | 0.85% (w/v) |
| Buffer system | Phosphates | 0.5% (w/v) |
| Detergents | Triton X100 ® | 0.05% (w/v) |
| (w/v) | Tween 20 ® | 0.0001% (v/v) |
| Ionophore | Valinomycin | 0.003% (w/v) |
| Stain | Thiazole orange | 0.005% (w/v) |
| Aldehyde | Paraformaldehyde | 1% (w/v) |

A sample of total blood is mixed with the above reagent solution. After an incubation of a few seconds (typically of the order of 15 to 30 seconds) the solution is analysed by means of a flow cytometry system comprising at least the following parameters: axial diffraction (FSC) providing an interpretation of the size, orthogonal diffusion (SSC) expressing the structure of the elements observed, and orthogonal fluorescence (FL1) enabling the expression of the intracellular ribonucleic acid to be measured.

The results thus obtained are observed in multidimensional mode so as to determine the interrelationships of the various populations among each parameter.

Reference will now be made to FIGS. 1 to 4, which show the results obtained with a sample of normal human blood.

Figure 1:
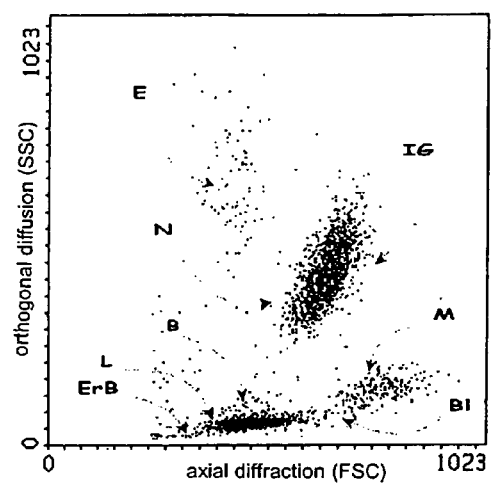
FIG. 1 illustrates a flow cytometric measurement of a blood sample.

FIG. 1 shows the matrix obtained by means of the two parameters, axial diffraction (FSC) and orthogonal diffusion (SSC). Four different populations can clearly be seen: L denotes lymphocytes, M denotes monocytes, N denotes polynuclear neutrophils, and E denotes polynuclear eosinophils. The populations IG of immature granulocytes, BL of blastocytes, B of polynuclear basophils and ErB of erythroblasts are shown but cannot be differentiated in only two dimensions.

Figure 2:
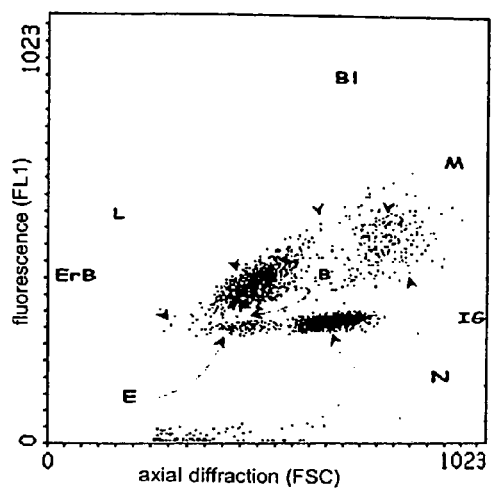
FIG. 2 illustrates a flow cytometric measurement of a blood sample.

FIG. 2 shows the matrix formed by the axial diffraction (FSC) and fluorescence (FL1) parameters. The same four populations as shown in FIG. 1 can be seen, but arranged differently. The mononucleate cells L and M form the upper group of average fluorescence, and the polymorphonucleate cells N, E and B form the lower group of weak fluorescence. The population ErB of erythroblasts is clearly separated at the apex of the two groups thus formed. The normal positions of the populations BL and IG are shown.

Figure 3:
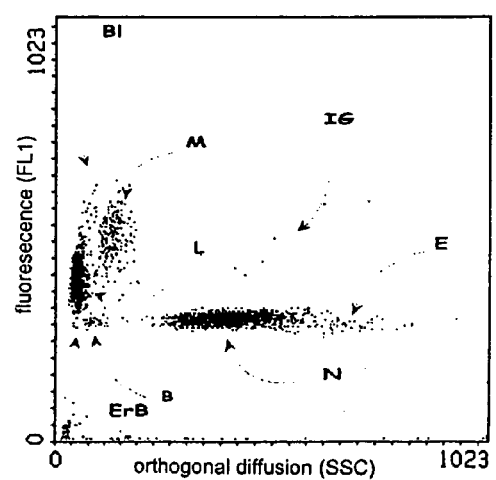
FIG. 3 illustrates a flow cytometric measurement of a blood sample.

FIG. 3 shows the matrix formed by the orthogonal diffusion (SSC) and fluorescence (FL1) parameters. The same populations are found organised in a different way, but enabling the populations IG and BL to be isolated (in very small amounts in a normal sample).

Figure 4:
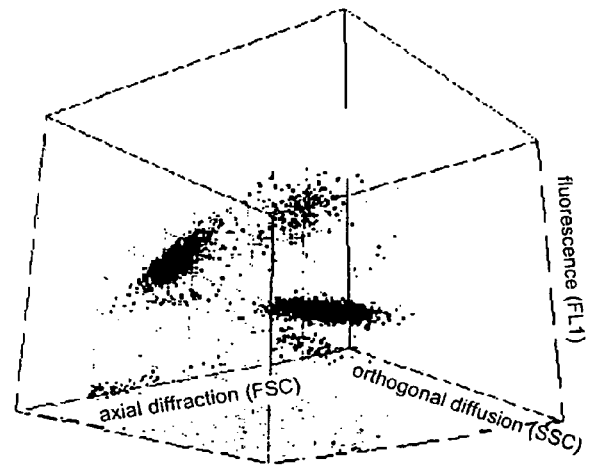
FIG. 4 illustrates a flow cytometric measurement of a blood sample.

FIG. 4 shows a three-dimensional representation of the populations obtained.

Figure 5:
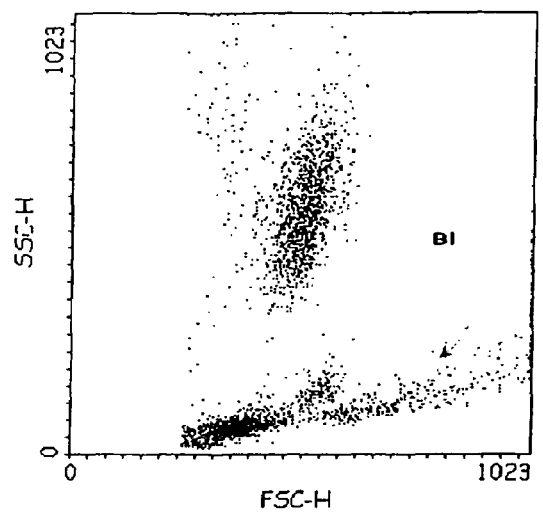
FIG. 5 illustrates a flow cytometric measurement of a blood sample having blast cells.
Figure 6:
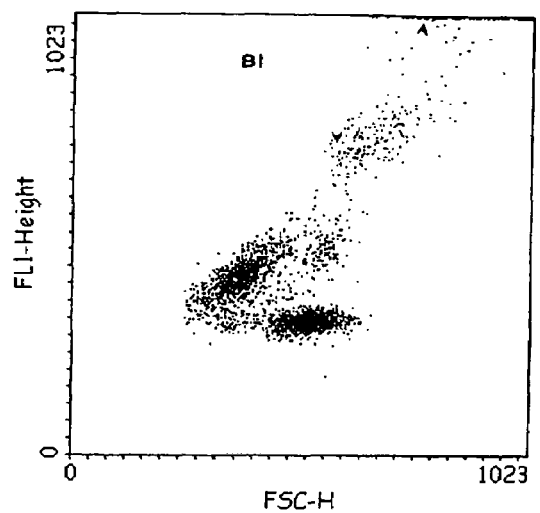
FIG. 6 illustrates a flow cytometric measurement of a blood sample having blast cells.
Figure 7:
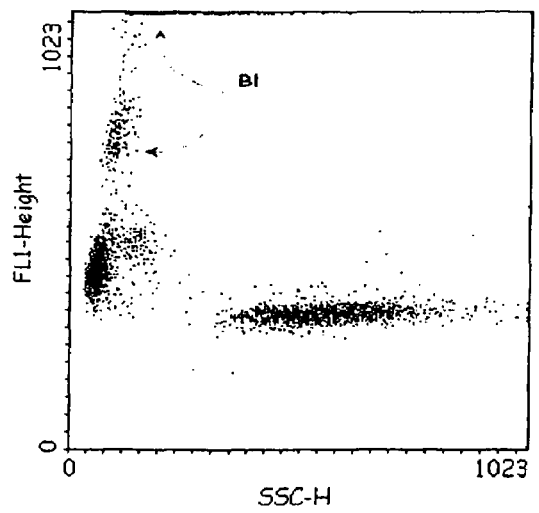
FIG. 7 illustrates a flow cytometric measurement of a blood sample having blast cells.
Figure 8:
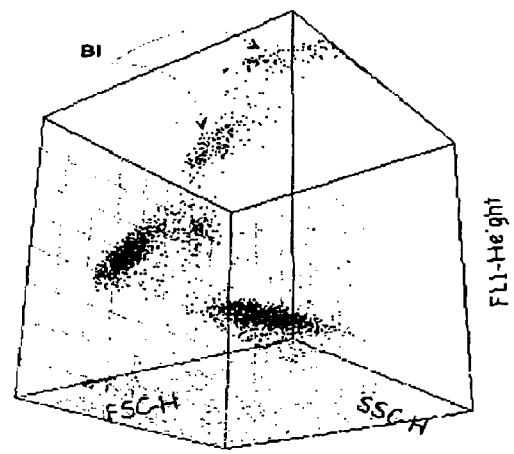
FIG. 8 illustrates a flow cytometric measurement of a blood sample having blast cells.
Figure 9:
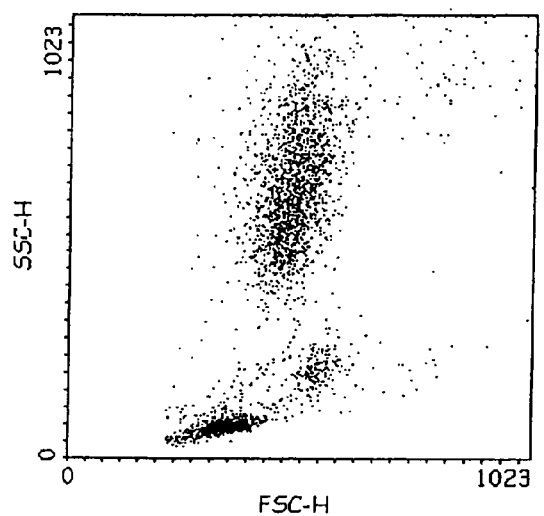
FIG. 9 illustrates a flow cytometric measurement of a blood sample having immature granulocytes.
Figure 10:
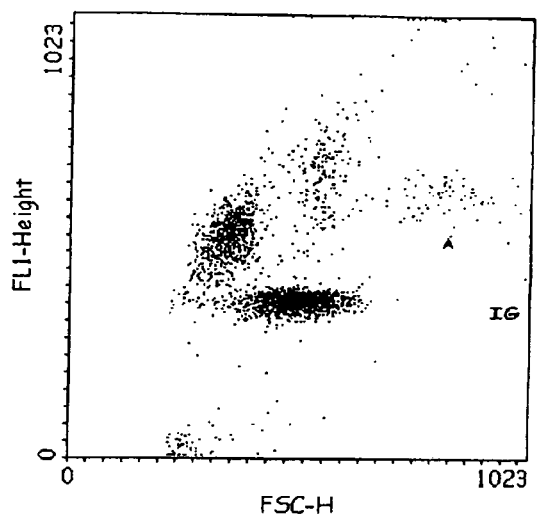
FIG. 10 illustrates a flow cytometric measurement of a blood sample having immature granulocytes.
Figure 11:
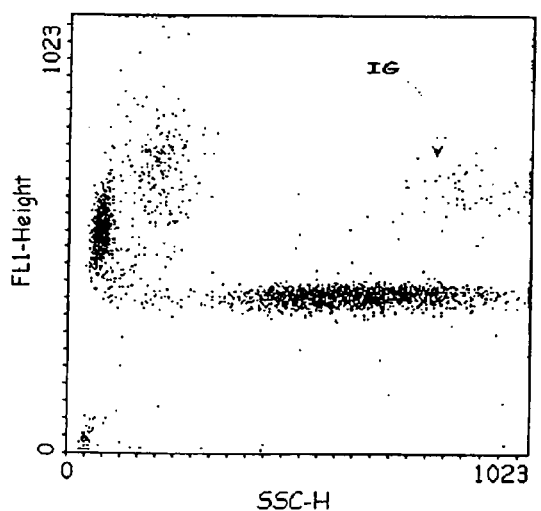
FIG. 11 illustrates a flow cytometric measurement of a blood sample having immature granulocytes.
Figure 12:
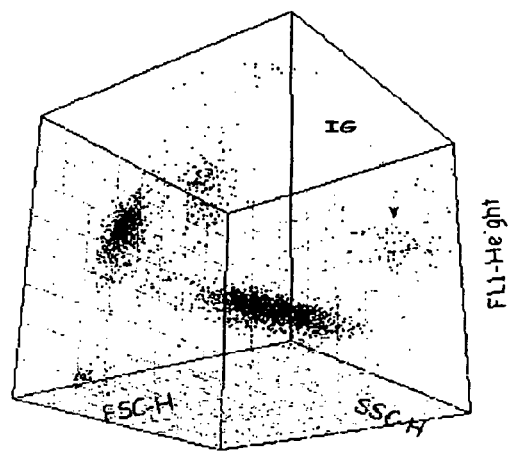
FIG. 12 illustrates a flow cytometric measurement of a blood sample having immature granulocytes.

FIGS. 5 and 8 show the same types of results as FIGS. 1 to 4 respectively, but obtained with a sample containing blast cells (B1) and treated according to the invention.

FIGS. 9 to 12 show the same types of results as FIGS. 1 to 4 respectively, but obtained with a sample containing immature granulocytes (IG) and treated according to the invention.

The reagent and the process of the invention thus enable a specific lysis and a simultaneous staining of biological cells in a sample, in particular in a sample of human or animal blood, to be carried out in a single stage.

Cells may thus be identified and counted rapidly using an automated analysis system based on flow cytometry.

The invention claimed is:

1. A process for the identification and counting of biological cells in a sample comprising erythrocytes, the process comprising the following operations in a single stage:
    simultaneously lysing the erythrocytes by mixing and incubating the sample with a cell lysing agent comprising at least one detergent in a concentration capable of specifically lysing erythrocytes in the sample at least one membrane fixing agent, and a membrane penetration agent selected from the group consisting of an ionophore compound of the protonophore type, an ionophore of the antibiotic type, and a mixture of ionophores, and
    staining intracellular nucleic acids of unlysed cells,
    to provide a mixture of lysed erythrocytes and unlysed cells having stained intracellular nucleic acids, and
    identifying and counting the unlysed cells by flow cytometry using at least two measuring parameters selected from the group consisting of resistive volume, axial luminous diffraction, axial luminous transmission, orthogonal light scattering, and fluorescence.

2. The process according to claim 1, wherein the cell lysing agent comprises at least one ionic and/or non-ionic detergent in a concentration capable of lysing erythrocytes.

3. The process according to claim 1, wherein the detergent is selected from the group consisting of:
    primary amines, amine acetates and hydrochlorides, quaternary ammonium salts, and trimethylethyl ammonium bromide;
    amides of substituted diamines, diethanolamino-propylamine or diethylaminopropylamide, amides of cyclised diethylenetriamine;
    alkylaryl sulfonates, petroleum sulfonates, sulfonated glycerides;
    cholamides, sulfobetaines;
    alkyl glycosides, saponins;
    polyoxyethylene ethers and sorbitans, and polyglycol ethers.

4. The process according to claim 1, wherein the stain is a fluorescent type stain.

5. The process according to claim 1, wherein the stain is capable of combining specifically with intracellular ribonucleic acid of said unlysed remaining cells whereby the fluorescence of said stain is enhanced.

6. The process according to claim 1, wherein the stain is selected from the group consisting of:
    thiazole orange or 1-methyl-4-[(3-methyl-2-(3H)-benzothiazolylidene)methyl]quinolinium p-tosylate,
    thiazole blue,
    4-[(3-methyl-2-(3H)-benzothiazolyl-idene)methyl]-1-[3-(trimethylammonium)propyl]quinolinium diiodide,
    3,3'-dimethyloxacarbocyanine iodide or 3-methyl-2-[3-(3-methyl-2(3H)-benzothiazolylidene-1-propenyl]benzoxazolium iodide,
    thioflavine T,
    the stains SYTO® and TOTO® (TM Molecular Probes),
    ethidium bromide,
    propidium iodide,
    acridine orange,
    coriphosphine O,
    auramine O,
    the stains 2'-(4-hydroxyphenyl)-5-(4-methyl-1-piperizinyl)-2,5'-bi-1H-benzimidazole trihydrochloride hydrate and 2'-(4-ethoxyphenyl)-5-(4-methyl-1-piperizinyl)-2,5'-bi-1H-benzimidazole trihydrochloride,
    4',6-diamino-2-phenylindole dihydrochloride (DAPI),
    4',6-diimidazolin-2-yl)-2-phenylindole dihydrocholoride (DIPI),
    7-aminoactinomycin D,
    actinomycin D, and
    LDS 751 (2-(4-(4-dimethylaminophenyl)-1,3-butadienyl)-3-ethylbenzothiazolium perchlorate).

7. The process according to claim 1, wherein the at least one membrane fixing agent is present in a concentration of 0.1% to 10% (w/v).

8. The process according to claim 7, wherein the membrane fixing agent comprises at least one alcohol or at least one aldehyde selected from the group consisting of paraformaldehyde and glutaraldehyde, or a mixture of at least one said alcohol and at least one said aldehyde.

9. The process according to claim 1, wherein the cell lysing agent also comprises at least one compound selected from the group consisting of a complexing agent, an inorganic salt and a buffer system.

10. The process according to claim 1, wherein the resistive volume measurement is carried out by application of any one of a continuous current, a pulsed current, or an alternating current.

11. The process according to claim 1, wherein the axial luminous diffraction parameter is at least one parameter selected from the group consisting of small angle diffraction and large angle diffraction.

12. The process according to claim 1, wherein the unlysed cells having stained intracellular nucleic acids are either mature or immature, normal or abnormal cells.

13. The process according to claim 1, further comprising classifying the unlysed cells by means of a multidimensional analysis software program, with or without the use of a software or other neuronal technique.

14. The process according to claim 1, wherein the sample is a sample of human or animal blood.

15. The process according to claim 1, wherein the sample is a sample of biological fluid or a suspension of cells of human or animal origin.

* * * * *